US009649073B2

(12) United States Patent
King et al.

(10) Patent No.: US 9,649,073 B2
(45) Date of Patent: May 16, 2017

(54) USAGE MODELING FOR INTELLIGENT MANAGEMENT OF ALARMS AND MESSAGES IN MOBILE HEALTH SYSTEMS

(71) Applicant: Voalte, Inc., Sarasota, FL (US)

(72) Inventors: Benjamin King, University Park, FL (US); Sethumadavan Sanjay-Gopal, Viera, FL (US); Michael G. Sica, Orlando, FL (US); Philip N. Fibiger, Winter Park, FL (US); Donnie C. Fletcher, Sarasota, FL (US)

(73) Assignee: Voalte, Inc., Sarasota, FL (US)

( * ) Notice: Subject to any disclaimer, the term of this patent is extended or adjusted under 35 U.S.C. 154(b) by 0 days.

(21) Appl. No.: 14/485,750

(22) Filed: Sep. 14, 2014

(65) Prior Publication Data

US 2016/0078750 A1 Mar. 17, 2016

(51) Int. Cl.
| | | |
|---|---|---|
| G08B 29/00 | (2006.01) | |
| A61B 5/00 | (2006.01) | |
| G06F 19/00 | (2011.01) | |
| A61B 5/0205 | (2006.01) | |
| A61B 5/11 | (2006.01) | |

(52) U.S. Cl.
CPC ........... *A61B 5/746* (2013.01); *A61B 5/002* (2013.01); *G06F 19/327* (2013.01); *A61B 5/0205* (2013.01); *A61B 5/1113* (2013.01); *A61B 5/1115* (2013.01); *A61B 5/747* (2013.01)

(58) Field of Classification Search
None
See application file for complete search history.

(56) References Cited

U.S. PATENT DOCUMENTS

| | | | |
|---|---|---|---|
| 9,129,501 B1 | 9/2015 | King et al. | |
| 2005/0200488 A1* | 9/2005 | Riley | G08B 21/0469 340/573.4 |
| 2008/0275349 A1* | 11/2008 | Halperin et al. | 600/484 |
| 2009/0018882 A1* | 1/2009 | Burton et al. | 705/7 |
| 2009/0247848 A1* | 10/2009 | Baker, Jr. | 600/323 |
| 2010/0225501 A1* | 9/2010 | Grubis et al. | 340/870.16 |
| 2010/0262430 A1* | 10/2010 | Gips | G06F 19/327 705/2 |
| 2011/0202495 A1* | 8/2011 | Gawlick | 706/59 |
| 2012/0169467 A1* | 7/2012 | Condra | 340/8.1 |
| 2012/0244834 A1* | 9/2012 | Behairy et al. | 455/406 |
| 2014/0132413 A1* | 5/2014 | Fox et al. | 340/573.1 |
| 2014/0292517 A1* | 10/2014 | Hu et al. | 340/573.1 |

* cited by examiner

*Primary Examiner* — Curtis King
(74) *Attorney, Agent, or Firm* — Long Technology Law, LLC; Joseph L. Long

(57) ABSTRACT

Systems and methods can support usage modeling and the intelligent management of patient alarms. An alarm management system can maintain models of patient alarm operations. Modeling parameters related to clinical user behavior and modeling parameters related to alarm context can be incorporated into the models of patient alarm operations. The models of patient alarm operations can inform rules associated with intelligent alarm management. The rules may be applied to the presentation of alarms to the clinical users via mobile computing devices. The rules may also be applied to the interpretation of alarm responses from the clinical users. The rules may be adapted by the alarm management system to improve metrics of alarm efficacy and/or metrics of patient health outcomes.

20 Claims, 9 Drawing Sheets

USAGE MODELING FOR INTELLIGENT MANAGEMENT OF ALARMS AND MESSAGES IN MOBILE HEALTH SYSTEMS

BACKGROUND

Various instruments and events within a healthcare enterprise can generate alarms for notifying point-of-care staff such as nurses and physicians of event and conditions of concern regarding patients. As more systems in the healthcare enterprise become computerized and networked, electronic alarms become more and more numerous and frequent. As clinicians become desensitized to frequent interruptions of these alarms, they often begin to ignore the alarms or even turn them off. This phenomenon is referred to as alarm fatigue.

Alarms should ideally be routed to the correct staff member. This is often complicated by staff assignment updates or modifications due to shift changes. Furthermore, alarms are not always routed to the most proximate, available, or appropriately skilled staff member to handle the alarm.

There is a need in the art for healthcare enterprise alarm and event management technologies that can intelligently impact the presentation and acknowledgement of alarms, messages, and notifications to improve patient outcomes and reduce costs.

SUMMARY

In certain example embodiments described herein, methods and systems can support usage modeling and the intelligent management of patient alarms. An alarm management system can maintain models of patient alarm operations. Modeling parameters related to clinical user behavior and modeling parameters related to alarm context can be incorporated into the models of patient alarm operations. The models of patient alarm operations can inform rules associated with intelligent alarm management. The rules may be applied to the presentation of alarms to the clinical users via mobile computing devices. The rules may also be applied to the interpretation of alarm responses from the clinical users. The rules may be adapted by the alarm management system to improve metrics of alarm efficacy and/or metrics of patient health outcomes.

These and other aspects, objects, features, and advantages of the example embodiments will become apparent to those having ordinary skill in the art upon consideration of the following detailed description of illustrated example embodiments.

DETAILED DESCRIPTION OF EXAMPLE EMBODIMENTS

Overview

The technology presented herein can significantly improve the efficacy of various alarms, messages, and notifications within a healthcare enterprise to improve patient outcomes and reduce costs. The technology can leverage machine intelligence to collect, aggregate, evaluate, process, and model data to enable the intelligent presentation and acknowledgement of alarms, events, alerts, and messages between various combinations of caregivers, instrumentation, and information systems. The machine intelligence can extend to modeling, predicting, and optimizing behaviors of users as individuals or according to various roles and/or assignments. Application of this technology can reduce alarm fatigue while improving the delivery and routing of alarms. Acknowledgment or response to alarms may also be improved through the application of the technology presented herein.

The functionality of the various example embodiments will be explained in more detail in the following description, read in conjunction with the figures illustrating the program flow. Turning now to the drawings, in which like numerals indicate like (but not necessarily identical) elements throughout the figures, example embodiments are described in detail.

Example System Architectures

Figure 1:
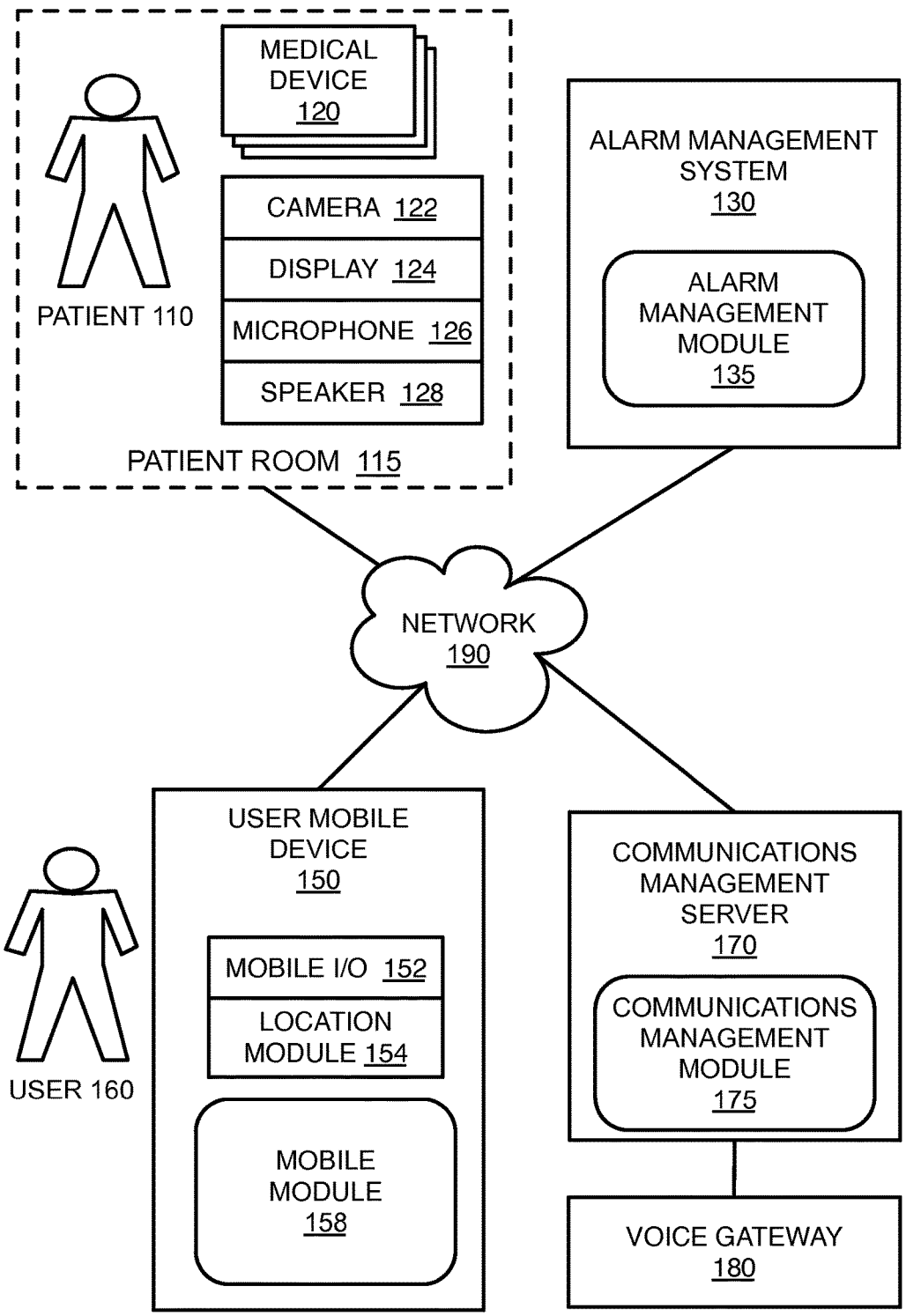
FIG. 1 is a block diagram depicting an alarm management system within a healthcare enterprise in accordance with one or more embodiments presented herein.

FIG. 1 is a block diagram depicting an alarm management system 130 within a healthcare enterprise in accordance with one or more embodiments presented herein. The alarm management system 130 can execute one or more alarm management modules 135 to process alarm events associated with a patient 110. The alarms may originate from medical devices 120 in the patient room 115 or otherwise associated with the patient 110. The patient room 115 may also incorporate a camera 122, video display 124, microphone 126, speaker 128, other sensors, or other input/output devices configured to communicate with or relay information associated with the patient 110. Alarm information may be communicated to a user 160 within a healthcare enterprise via a user mobile device 150. The user mobile device 150 can execute one or more mobile modules 158. The user mobile device 150 can leverage various mobile input/output (I/O) 152 modalities such as touch screens, microphones, speakers, video displays, and so forth. The user mobile device 150 can also incorporate one or more location modules 154 for determining location and motion. A communication management server 170 may execute one or more communication management modules 175 to coordinate communication between the patient 110, alarm management system 130, and user 160. This communication may include voice or video calls coupled through a voice gateway 180. The patient 110, associated medical devices 120, alarm management system 130, user 160, associated user mobile device 150, communication management server 170, and other various system elements may be in data communications through one or more networks 190.

The medical devices 120 in the patient room 115 or otherwise associated with the patient 110 may include various monitors or telemetry devices. For example, the medical devices 120 may include heart monitors, respiration monitors, blood pressure monitors, blood oxygen sensors, intravenous delivery systems, pain management systems, fetal monitors, and so forth. The medical devices 120 may also include smart beds that can report patient movement, when the patient exits or enters, when the guardrails have moved, and other such specifics. Similarly, the medical devices 120 may include a call button at the bed or in the restroom, motion sensors, communications devices, and so forth. Any of these, or other such, medical devices 120 can generate alarms or alarm indicators for a variety of reasons. Generally, the alarms are generated when a certain condition obtains such as a measurement threshold being exceeded or a sensor or switch being activated.

The alarm information generated by the medical devices 120 may be relayed from the medical devices 120 to the alarm management system 130 for presentation to one or more users 160. The alarms may be communicated using Wireless Communications Transfer Protocol (WCTP), WiFi, XML, HTTP, TCP/IP, or various other networking protocols, technologies, or topologies. These communications may follow one or more messaging standards that define how information is packaged and communicated from one system to another. Such standards can specify languages, structures, and/or data types for integrating information between systems. An example of such a standard is Health Level Seven (HL7), which includes a set of rules for information to be shared and processed in a uniform and consistent manner within the healthcare enterprise.

The patient room 115 may include communications or monitor devices. These may include a camera 122, a video display 124, a microphone 126, a speaker 128, or various other sensors. The microphone 126 and speaker 128 can support voice communications or intercom functionality. Addition of a camera 122 and/or video display 124 can support video monitoring or even video conferencing. For example, a user 160 can communicate with, listen to, or visually observe the patient 110 from a user mobile device 160 or other computing machine or communication device. For example, the patient may be visually monitored from a computer display at a nurse station. The various communication modalities may be supported by the communication management server 170 and may interface through the voice gateway 180 to existing voice communication systems (such as VoIP, PBX, or POTS systems) or similar video conferencing systems.

One example use case for real-time audio/video communication between the patient 110 and the user 160 can provide timely response when the patient 110 could potentially be falling out of their bed in a hospital or other care facility. Using video conferencing devices in the patient room 115, a view of the room may be transmitted to the user 160 assigned to that particular patient 110. According to one or more example embodiments, the user 160 may be a nurse that is currently in a different area of the unit or hospital. The user 160 can also obtain a complete visual on their user mobile device 150 showing the patient's condition in the room on demand at any time. The user 160 could remotely warn the patient 110. If close enough to the patient 110, the user 160 could rush to the room to either prevent the patient 110 from falling or catch the patient 110 during the fall to lower adverse impact. The user 160 could alternatively escalate the alarm situation to other users 160 (care providers) who may be closer to the patient 110. To support devices in the patient room 115, such as the camera 122 and microphone 126, to transmit live video and audio to the user 160, the alarm management system 130 can identify the user 160 who is assigned to the particular patient 110. The alarm management system 130 can track the location of various users 160 to determine who may be currently closest to the potentially falling patient 110.

The user 160 may be a care provider in a hospital or other care facility. The user 160 may be a nurse, physician, therapist, technician, assistant, specialist, or any other care provider. The user 160 can interface with a user mobile device 150 for receiving presentation of, and responding to, alarm notifications or related messages. The user 160 can receive other information related to the patient 110 via the user mobile device 150. This other information may include voice or video communications, data strips from medical devices 120, and of forth. The mobile modules 158 can provide software, firmware, or hardware for executing the functionality of the user mobile device 150 as discussed herein. The mobile I/O 152 can include various sensors, input, and output mechanisms associated with the user mobile device 150. These may include touch screens, microphones, speakers, video displays, and so forth. The location module 154 can provide the user mobile device 150 with location awareness for use within the user mobile device 150 or relaying to the alarm management system 130. The location modules 154 can include GPS, beacon locating, wireless access point positioning, RTLS, or other mapping/location services. Wireless access point positioning can determine the location of the user mobile device 150 based upon which wireless access points it is currently able to connect with and possibly what their respective apparent power levels read as.

It should be appreciated that the user 160 may also interface through a desktop computer or workstation instead of a user mobile device 150. For example, the user 160 may be using a desktop computer system in the office or at a nurse's station in a hospital or other care facility.

The alarm management system 130, in conjunction with the alarm management modules 135, as well as the other systems and modules presented herein can operate to perform the functionality discussed in association with the present technology. While traditional middle-wear may have directly presented any generated alarms without evaluation, aggregation, or processing. This functionality is provided by the technology presented herein. This technology may be referred to as "smart alarms" or "intelligent alarms." It should be appreciated that in addition to the alarm management modules 135, mobile modules 158, communication management modules 175, the technology presented herein may include or interface with various other modules. It should also be appreciated that any two or more of these modules may be combined into the same module or modules. Furthermore, any one or more of these modules may split functionally, or load share, between two or more modules or execute on two or more computing machines. Any such modules may operate in a parallel, distributed, or networked fashion without departing from the spirit or scope of the technology presented herein. The functionality presented herein may be implanted at the patient room 115, the alarm management system 130, the user mobile device 150, or in a combination of two or more of those locations. Peer-to-peer communication may also be supported between multiple user mobile devices 150.

Figure 9:
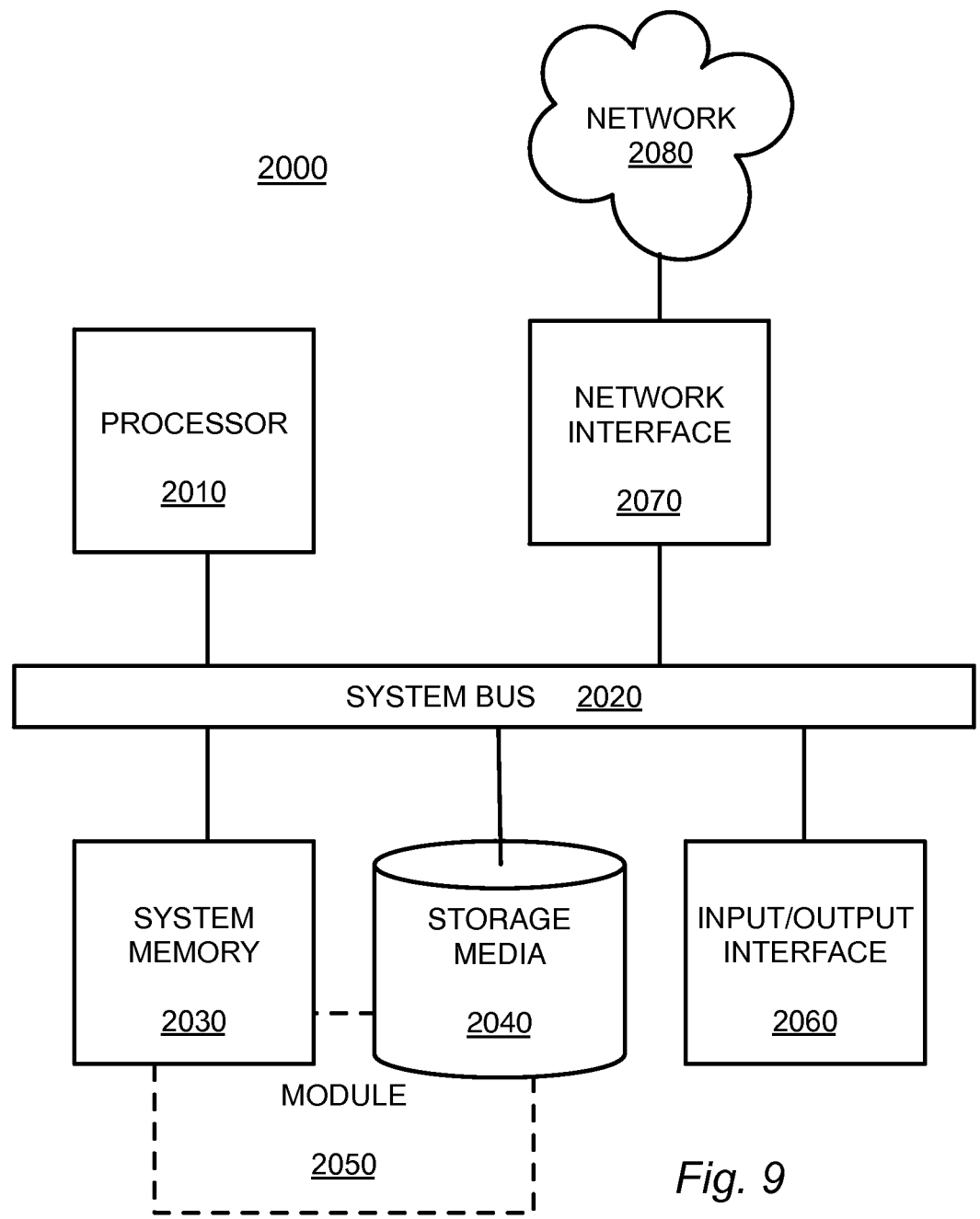
FIG. 9 is a block diagram depicting a computing machine and a module in accordance with one or more embodiments presented herein.

The alarm management system 130, user mobile device 150, communication management server 170, systems associated with the patient room 115, other systems associated with the users 160, or any other systems associated with the technology presented herein may be any type of computing machine such as, but not limited to, those discussed in more detail with respect to FIG. 9. Furthermore, any modules (such as the alarm management modules 135, mobile modules 158, communication management modules 175) associated with any of these computing machines or any other modules (scripts, web content, software, firmware, or hardware) associated with the technology presented herein may by any of the modules discussed in more detail with respect to FIG. 9. The computing machines discussed herein may communicate with one another as well as other computer machines or communication systems over one or more networks such as network 190. The network 190 may include any type of data or communications network including any of the network technology discussed with respect to FIG. 9.

Figure 2:
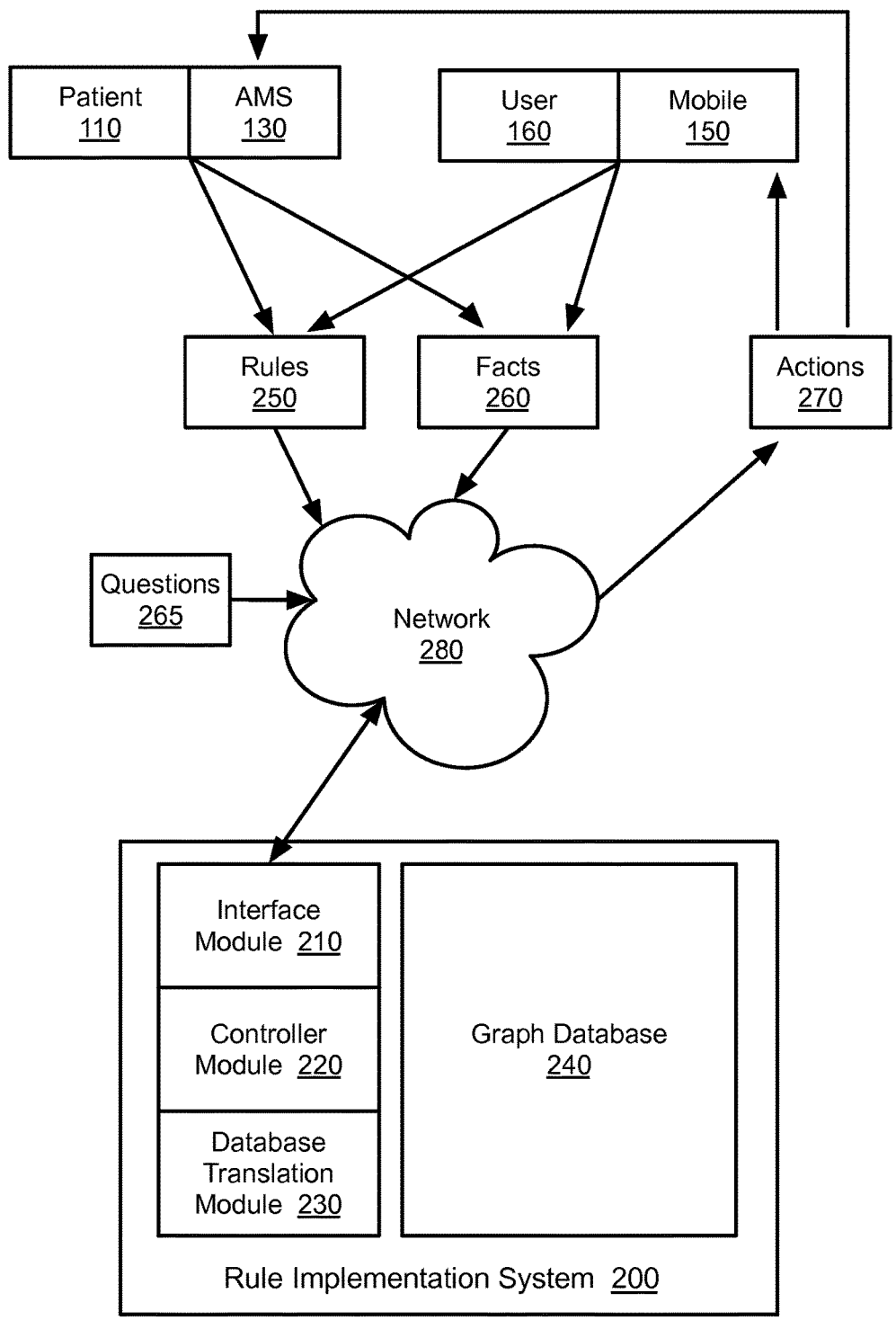
FIG. 2 is a block diagram depicting the application of a rule implementation system with an alarm management system in accordance with one or more embodiments presented herein.

FIG. 2 is a block diagram depicting the application of a rule implementation system 200 with an alarm management system 130 in accordance with one or more embodiments presented herein. The rule implementation system 200 can operate on rules 250 and facts 260 to respond to questions 265 or to establish additional rules 250, additional facts 260, or trigger actions 270. At the alarm management system 130 and the user mobile device 150, the actions 270 can inform alarm processing associated with the patient 110 and the user 160. The rule implementation system 200 can include various modules such as an interface module 210, a controller module 220, and a database translation module 230. The rule implementation system 200 can operate directly within, or in conjunction with, a graph database 240. Rules 250, facts 260, questions 265 or actions 270 associated with the rule implementation system 200 may be communicated directly to or from the rule implementation system 200. These communications may also occur in conjunction with one or more networks 280.

While the rule implementation system 200 is illustrated as broken out from the alarm management system 130, it should be appreciated that the rule implementation system 200 may operate as one or more modules associated with the alarm management system 130 (such as alarm management modules 135) according to various embodiments. According to various embodiments, the rule implementation system 200 may operate as one or more modules associated with the alarm management system 130 combined with one or more modules associated with the user mobile device 150 (such as mobile modules 158).

The rule implementation system 200 is an example of a rule engine system, production system, or production rule system. These are often used in artificial intelligence, automated planning, expert systems, action selection systems, or other such machine based knowledge or decision systems. For example, the rule implementation system 200 can implement the alarm processing associated intelligence associated with the alarm management system 130 and the user mobile device 150. The rule implementation system 200 can receive inputs (influencing or defining rules 250 and/or facts 260) from the alarm management system 130 and/or the user mobile device 150 indicating behavior of a user 160 or other related information such as their response patterns, locations, motion, and so forth.

A rule 250 associated with the rule implementation system 200 generally consists of two components: a condition and a result. The condition and result of a rule 250 may be said to have an "if, then" relationship. If the condition obtains, then the rule 250 is triggered causing the result to be fired. The condition generally obtains by the existence, or truth, of one or more facts 260. For example, a condition could be, "if it is Wednesday," which would trigger when presented with the fact that the day of the week is Wednesday. The result of firing a rule 250 generally involves one or more other facts 260 or the generation of an action 270. Firing of the rule 250 can assert or retract one or more other facts 260. Firing of the rule 250 can also generate one or more actions 270 as output of the rule implementation system 200. Asserting or retracting one or more facts 260 can alter the state of the rule implementation system 200, which may then affect the conditions of other rules 250 causing them to fire. Altering the state of the rule implementation system 200 may also affect the responses provided to questions 265 processed by the rule implementation system 200.

The rule implementation system 200 may also include a log, journal, or storage memory of events and/or status information. This log may provide a state or system memory for use in rule implementation. Accordingly, the rule implementation system 200 may function as a state machine responding to inputs in light of previous inputs, output, states, transition of states, or any combination thereof. Availability of such state information may be leveraged to provide complex event handling functionality in association with the rule implementation system 200.

The graph database 240 can provide the working memory of the rule implementation system 200. This working memory can store information comprising the current state or knowledge of the rule implementation system 200. The graph database 240 can store information in a graph structure where nodes are interconnected by edges. The nodes generally represent entities or things such as individuals, departments, or equipment. Edges generally connect nodes representing the relationship between them. Each node may be associated with one or more properties, which may contain information pertinent to that respective node. It should be appreciated that while various embodiments of the rule implementation system 200 may include a graph database 240 for storing and processing rules 250 and/or facts 260, other types and structures of storage or association may be used to implement the same functionality without departing from the scope of the technology presented herein.

The interface module 210 of the rule implementation system 200 can provide an application programming interface (API), scripting interface, domain-specific language (DSL), or other mechanism for interfacing to the rule implementation system 200. The interface module 210 may support transactions with other modules, systems, or entities associated with the rule implementation system 200. These transactions may involve providing rules 250 or facts 260 to the rule implementation system 200, receiving and reacting to questions 265, retrieving rules 250 or facts 260 from the rule implementation system 200, or receiving actions 270 or information associated with actions 270 from the rule implementation system 200.

The controller module 220 of the rule implementation system 200 can process control operations of the rule implementation system 200. Examples of the operations may include executing queries, starting/stopping rule evaluation, and so forth.

The database translation module 230 of the rule implementation system 200 can provide low-level interactions with the graph database 240. These interactions may include performing queries, handling fact node assertion or retraction, database administrative tasks, and so forth.

It should be appreciated that in addition to the interface module 210, controller module 220, database translation module 230, and graph database 240, the rule implementation system 200 may include or interface with other modules. It should also be appreciated that any two or more of these modules may be combined into the same module or modules. Furthermore, any one or more of these modules may split functionally, or load share, between two or more modules or execute on two or more computing machines. Any such modules may operate in a parallel, distributed, or networked fashion without departing from the spirit or scope of the technology presented herein.

A domain-specific language (DSL) may be used to simplify the specification of rules 250 and/or facts 260 to the rule implementation system. For example, a DSL designed for pharmacists or for specifying pharmaceutical prescriptions may be used to allow entry of prescription details in natural (or nearly natural) human languages, such as "prescribe 81 mg aspirin each morning to cardiac patients," and "do not prescribe aspirin to patients taking blood thinning medication." A specific DSL may be tuned to one or more specific areas of patient care have specific subsets of language or jargon. For example, surgery, physical rehab, radiology, etc. A DSL may also be defined for specifying system functions such as call rules, message rules, alarm routing, alarm filtering, alarm responses, alarm escalation, or other alarm related processes. For example, a DSL may allow a nurse to enter a rule from "send me an alarm if patient in room 222 attempts to exit their bed or if their heart rate exceeds 130 BPM," which may be followed by "offer those alarm settings to next responsible nurse when my shift ends." The inputs may be entered as text or converted to text from speech entered by the user 160. The inputs may be entered by the user 160 at the user mobile device 150 or any other system accessed, directly or indirectly, by the user 160.

The rule implementation system 200, systems associated with the rules 250, facts 260, or actions 270, or any other systems associated with the technology presented herein may be any type of computing machine such as, but not limited to, those discussed in more detail with respect to FIG. 9. Furthermore, any modules (such as the interface module 210, controller module 220, or database translation module 230) associated with any of these computing machines or any other modules (scripts, web content, software, firmware, or hardware) associated with the technology presented herein may by any of the modules discussed in more detail with respect to FIG. 9. The computing machines discussed herein may communicate with one another as well as other computer machines or communication systems over one or more networks such as network 280. The network 280 may include any type of data or communications network including any of the network technology discussed with respect to FIG. 9.

Figure 3:
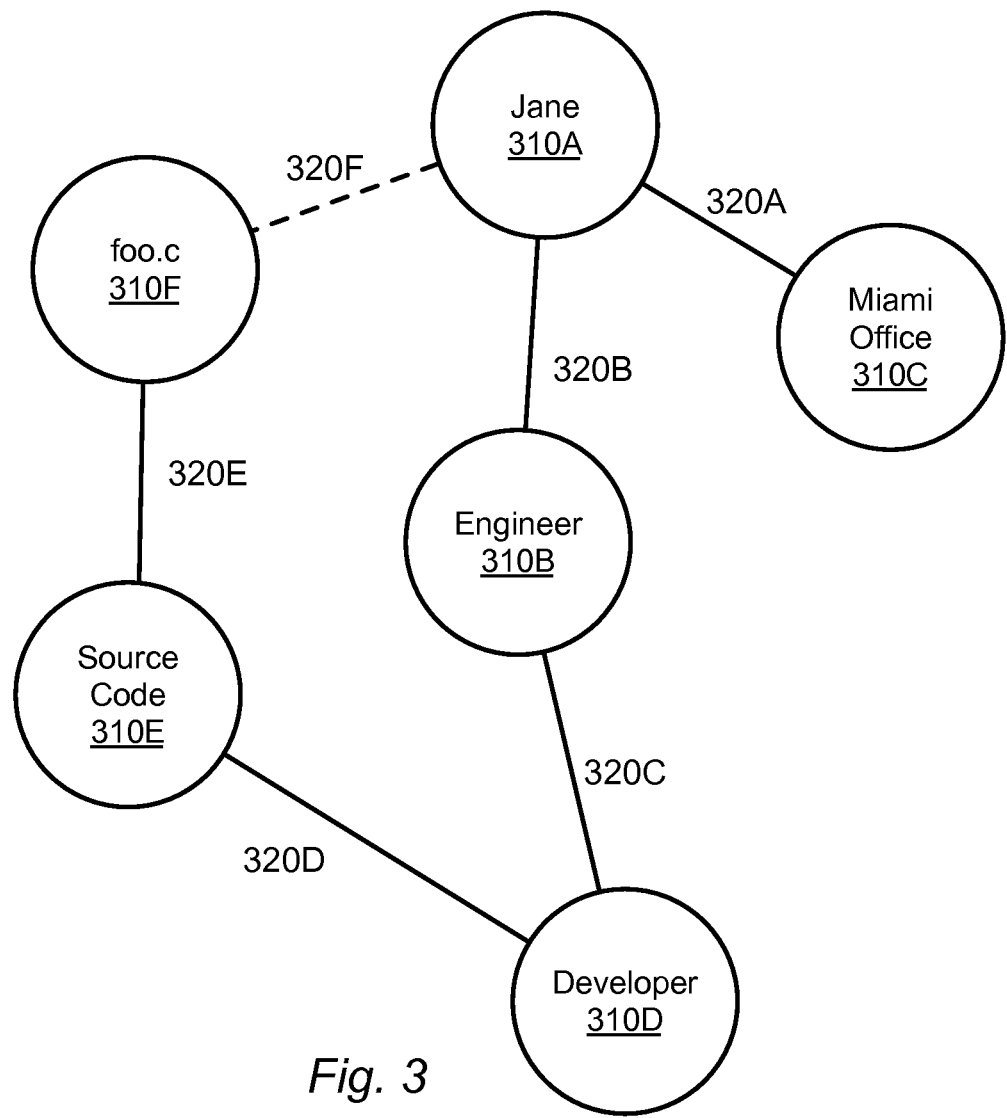
FIG. 3 is an example data structure diagram illustrating a rule-fact graph associated with a rule implementation system in accordance with one or more embodiments presented herein.

FIG. 3 is an example data structure diagram illustrating a rule-fact graph 300 associated with a rule implementation system 200 in accordance with one or more embodiments presented herein. The illustrated rule-fact graph 300 is a simplified example of a graph that may be stored in the graph database 240 of the rule implementation system 200.

The rule-fact graph 300 includes nodes 310A-310F connected by edges 320A-320F. The nodes 310A-310F may be referred to collectively or in general as nodes 310. Similarly, the edges 320A-320F may be referred to collectively or in general as edges 320.

The rule-fact graph 300 within the graph database 240 can serve as the working memory of the rule implementation system 200. This working memory can store information comprising the current state or knowledge of the rule implementation system 200. This information can include various facts 260, which may be stored as nodes 310 connected by edges 320 representing relationships between the nodes 310 such that the nodes 310 and edges 320 together can encode rules 250.

Rule interpretation may be provided by executing queries on the rule-fact graph 300 within the graph database 240. The queries may be associated with questions 265 posed to the rule implementation system 200. The queries can pattern-match facts 260 against the encoded rules 250 determining which of the rules 250 to apply. The condition portion of each rule 250 may be tested against the current state of the working memory by pattern matching against the rule-fact graph 300. The consequent results can update the knowledge represented by the rule-fact graph 300 by asserting or retracting information. Rule interpretation can execute forward chaining when updated information affects other rules 250 implied within the rule-fact graph 300. The results consequent to the condition can also trigger actions 270. Queries of the rule-fact graph 300 within the graph database 240 can leverage a schema-free storage structure supporting index-free adjacency where any node 310 may be directly linked (by one or more edges 320) to its adjacent nodes 310 such that index lookups are unnecessary.

Considering the illustrated example rule-fact graph 300, node 310A represents the individual named "Jane" and the connection edge 320A between node 310A and the "Miami Office" node 310C can represent that the individual "Jane" works out of the "Miami Office." The connection edge 320B between node 310A and the "Engineer" node 310B can represent that the individual "Jane" has a role of "Engineer." The connection edge 320C between node 310B and the "Developer" node 310D can represent that those in the role of "Engineer" are also "Developers." The connection edge 320D between the "Developer" node 310D and the "Source Code" node 310E can represent a rule 250 that all "Developers" are given access to "Source Code." The connection edge 320E between the "Source Code" node 310E and the "foo.c" node 310F can represent that source code file "foo.c" is and instance of "Source Code."

An example rule interpretation can deduce edge 320F between the "foo.c" node 310F and the individual "Jane" node 310A from the rule 250 that all "Developers" are given access to "Source Code" combined with the fact 260 that "Jane" is an "Engineer" and thus a "Developer." This deduced relationship associated with edge 320F may be the basis for returning "foo.c" as an answer to the question 265 "What source code files does Jane have access to?" The deduced relationship associated with edge 320F may also be the basis for returning "Jane" as an answer to the question 265 "Who has access to the file foo.c?" According to certain embodiments, the deduced relationship associated with edge 320F can persist in the memory of the rule-fact graph 300 until some other rule interpretation or operation on the graph database 240 retracts it.

Representing rules 250 within the graph database 240 provide the ability to establish adjacencies between any nodes 310 (and thus relationships between facts 260) without having to rebuild schemas or introduce associating tags or indices. Accordingly, rules 250 may be changed or introduced anew within the rule-fact graph 300 very efficiently and with reduced effort or overhead. For example in the illustrated rule-fact graph 300, if the rules that all developers have access to source code was changed to all engineers have access to source code, the connection edge 320D between the "Developer" node 310D and the "Source Code" node 310E would simply be moved to connect the "Engineer" node 310B and the "Source Code" node 310E. Changing this rule representation in a traditional database for a huge number of engineers/developers and/or a huge number of source code files could be extremely time consuming and nearly impossible, is such rules changed frequently as they might in certain complex enterprise environments such as health care information systems.

Further considering the example rule-fact graph 300 as illustrated, an example query for individuals adjacent to both the "Engineer" node 310B and the "Miami Office" node 310C can rapidly answer the question 265 of "which individuals in the Miami Office are engineers?"

The rule implementation system 200 and its rule-fact graphs 300 can provide the functionality and benefits of various graph-structured rule implementations, such as the Rete Algorithm, along with additional benefits for handling datasets and rule sets presenting the challenge of being any combination of very large, complex, dynamic, or unstructured.

Some examples of additional benefits to the rule implementation system 200 relate to it being more suitable for managing ad hoc and changing data with evolving schemas. For example, in a healthcare enterprise such as a hospital department, the number of nurses may vary from shift to shift, as might the number of patients. Furthermore, the roles of the nurses may change and the assignments relating the nurses to specific patients may also change. When additional facts 260 and rules 250 associated with the hospital department come into play, the rule-fact graph 300 can quickly become very large even while being dynamic (rapidly changing). For example, the additional facts 260 and rules 250 may relate to procedures, medications, food service, radiology, tests, specialist referrals, admit/discharges, code emergencies, monitoring alarms, and so forth. Other example additional facts 260 and rules 250 may relate to routing messages, alarms, notifications, voice calls, text messages, or other communication modalities to one or more nurses (or wireless mobile devices associated therewith) within a healthcare enterprise. This type of information is also well addressed by the schema-less structure support of the rule implementation system 200 and its associated graph database 240.

Another example benefit to the rule implementation system 200 stems from the native pattern matching capabilities of the rule implementation system 200 and its associated graph database 240. Such native pattern matching support can provide for significant increases in efficiencies related to rule interpretation and associated queries.

Yet another example benefit to the rule implementation system 200 relates to the disk-backed performance of the rule implementation system 200 and its associated graph database 240. Disk-backed operation can provide persistence of state by maintain information within the graph database 240. Disk-backed operation can also overcome working memory limitations encountered in operating on a rule-fact graph 300 of ever increasing size and complexity.

Example Processes

According to methods and blocks described in the embodiments presented herein, and, in alternative embodiments, certain blocks can be performed in a different order, in parallel with one another, omitted entirely, and/or combined between different example methods, and/or certain additional blocks can be performed, without departing from the scope and spirit of the invention. Accordingly, such alternative embodiments are included in the invention described herein.

Figure 4:
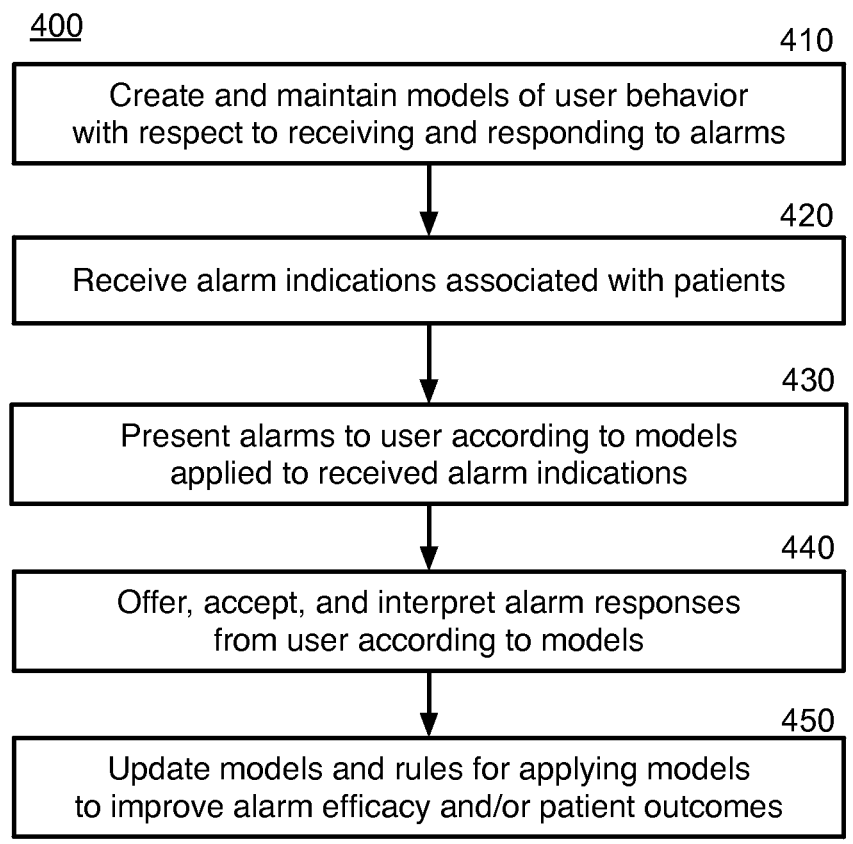
FIG. 4 is a block flow diagram depicting a method for alarm management within a healthcare enterprise in accordance with one or more embodiments presented herein.

FIG. 4 is a block flow diagram depicting a method 400 for alarm management within a healthcare enterprise in accordance with one or more embodiments presented herein. In block 410, the alarm management system 130 can create and maintain models of user behavior with respect to receiving and responding to alarms. The models can incorporate information regarding how each user 160 (or category of users) reacts to various alarm scenarios given various pieces of contextual information.

In block 420, the alarm management system 130 can receive alarm indications associated with one or more patients 110. Alarms generated by the patient 110 or by associated medical devices 120 may be relayed to the alarm management system 130 as they occur. The alarm management system 130 can generate intelligent alarms by evaluating, aggregating, and/or processing alarm or alert conditions it receives and determining the proper resultant alarm signals to communicate to the users 160. Furthermore, the alarm management system 130 can process multiple alarms and/or incorporate multiple sources of other information to generate multivariate alarms. For example, an alarm from a patient monitor may be evaluated along with addition patient information from an electronic medical record (EMR) system or patient physiological information from one or more medical devices to generate a multivariate alarm. Also, the alarm management system 130 can apply models, statistical data, and information trends to predict future alarms. For example, various physiological data samples along with information about a recent invasive surgery may support the generation of a predictive alarm indicating that a patient may be entering a state of sepsis.

In block 430, the alarm management system 130 can present alarms to one or more users 160 according to models applied to received alarm indications. The models discussed with respect to block 410 can be applied to determine presentation of the alarms received in block 420. The determined presentation can include to whom (which user 160) and how the alarm is presented. Which user 160 the alarm is presented may be referred to as the target user 160. How the alarm is presented may be referred to as the modality of the alarm or alarm notification.

In block 440, the alarm management system 130 can offer, accept, and interpret alarm responses from the user 160 according to the models. The models discussed with respect to block 410 can be applied to the management of alarm responses associated with the alarms received in block 420. The models can assist in determining how an alarm may be responded too and then how to interpret the actual response received from the user 160 in association with the alarm.

In block 450, the alarm management system 130 can update models and rules 250 for applying models to improve alarm efficacy and/or patient outcomes. For example, one or more metrics of patient alarm efficacy may be defined where the metrics score how certain rules 250, operations, or parameters (such as thresholds or input weights) influence desirable patient outcomes. Patient outcomes may relate to physiological measurements, readmission rates, patient compliance evaluations, patient satisfaction ratings, and so forth. Adapting or updating a model can include, among other things, incorporating newly obtained data related to the model or processing the model in some updated fashion. Adapting rules 250 can include, among other things, selecting inputs to a rule; how those inputs are combined, weighted, or processed; and/or what thresholds are applied to those inputs.

The rules 250 can specify when and how to evaluate and incorporate various factors into models and associated decision-making processes. These factors may include the risk to patients when alarms malfunction or are not attended to. The factors may also include whether specific alarm signals are truly meaningful or instead unnecessarily contribute to alarm noise and alarm fatigue. The factors may also include specifying clinically appropriate settings for alarm signals. The factors may also include when alarm signals can be disabled or when alarm parameters can be changed. The factors may also include who in the organization has the authority to set alarm parameters, who in the organization has the authority to change alarm parameters, and/or who in the organization has the authority to disable alarm parameters. The factors may also include checking individual alarm signals for accurate settings, proper operation, and detectability.

Figure 5:
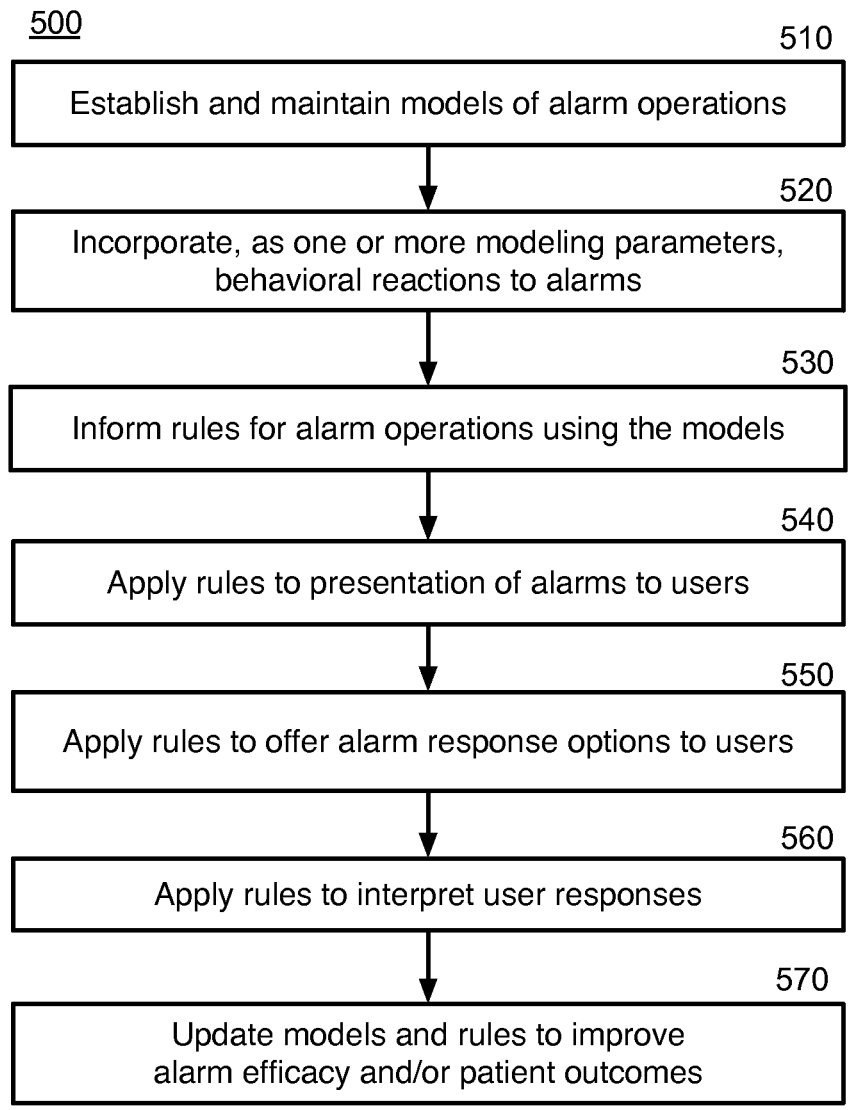
FIG. 5 is a block flow diagram depicting a method for modeling alarm operations within a healthcare enterprise in accordance with one or more embodiments presented herein.

FIG. 5 is a block flow diagram depicting a method 500 for modeling alarm operations within a healthcare enterprise in accordance with one or more embodiments presented herein. In block 510, the alarm management system 130 can establish and maintain models of alarm operations. The models can be maintained with respect to each individual user 160 as well as by classifications or groups of users 160 such as user roles, assignments, skill sets, schedules, or so on. The models may be represented as combinations of rules 250, facts 260, or state information associated with the rule implementation system 200 and/or the alarm management system 130. The models can comprise thresholds used when applying the rules. Such threshold may be applied to any input data used in the model.

In block 520, the alarm management system 130 can incorporate behavioral reactions to alarms as one or more modeling parameters. The behavioral reactions may relate to the location of the user 160, the location of the patient 110, the distance between the user 160 and patient 110, and/or the motion of the user 160 or the patient 110. For example, the behavior of a user 160 in reaction to various alarms may be modeled as a function of the location of the user 160, or the distance from the user 160 to the patient 110, or the motion of the user 160. For example, it may be determined through the use of behavior modeling that the user 160 generally moves towards the patient 110 almost immediately after receiving an alarm associated with that patient 110. Accordingly, the alarm management system 130 may note an instance where such motion does not begin within a certain time window as an implied rejection of the alarm by the user 160. Such location, distance, and motion models may be established with respect to individual users 160 or for categories of users such as roles, assignments, shifts, correlation to other patterns, and so forth. These models may be used to determine or evaluate the expected location of a user 160 from their current role or assignment. The location, distance, and motion parameters used in the modeling may be obtained from the location modules 154 associated with the user mobile device 150. Locations of patients 110 may be determined from provided floor maps of a facility (or coordinates, or distances associated therewith) along with the room and/or bed assignment information for the patient 110. It should be appreciated that motion information may also include information regarding changes in location, changes in motion, changes in changes in motion, and any other temporal or spatial derivatives (of any order) of position or location.

Also, the behavioral reactions may relate to the current activity of the user 160. For example, modeling may establish that when a user 160 is involved in a critical activity (such as a patient coding), the user 160 is very unlikely to respond to another alarm. Similarly, modeling may establish under what situations the user 160 responds in different ways, or at different urgencies, to various alarm types or indicator type. As another example, modeling may establish under what situations the user 160 responds in different ways, or at different urgencies when other alarms (and in what quantities) have recently been routed to the user 160.

In block 530, the alarm management system 130 can inform rules for alarm operations using the models. These may be rules 250 such as those associated with the rule implementation system 200. The models of when, how, and how rapidly various users 160 respond to what type of alarms along with facts 260 regarding the context of the users 160, the alarm conditions, and/or the context of the patient 110 may be used to intelligently manage to whom and how alarms are routed (or not) according to various contexts and inputs relevant to the established models. These deduction or implications established from models may be encoded into rules 250 such as those associated with the rule implementation system 200.

In block 540, the alarm management system 130 can apply rules 250 to presentation of alarms to users 160. The rules 250 may be those informed by the models as discussed with respect to block 520. According to some example embodiments, where modeling indicates that a particular user 160 is more likely to respond rapidly to an alarm when a particular alert tone is emitted from their user mobile device 150, a rule 250 may be established indicating for the preferred alert tone to be played when an alarm is routed to that user 160. This rule may be particularly effective when the alarm is critical or when nobody else is available to respond. Various other examples of applying rules for presenting alarms may be implemented according to various embodiments. Some of these example embodiments are discussed with respect to FIG. 6.

In block 550, the alarm management system 130 can apply rules to offer alarm response options to users 160. The rules 250 may be those informed by the models as discussed with respect to block 520. According to some example embodiments, where modeling indicates that patient outcomes are improved when users 160 who are cardiac care nurses are provided with an option to "accept and view heart monitor" for certain alarm conditions, a rule 250 may be established indicating for cardiac care nurses to optionally display the heart monitor data to their user mobile device 150 immediately upon acknowledging certain alarms. Various other examples of applying rules for alarms responses may be implemented according to various embodiments. Some of these example embodiments are discussed with respect to FIG. 7.

In block 560, the alarm management system 130 can apply rules to interpret user responses to alarms. The rules 250 may be those informed by the models as discussed with respect to block 520. According to some example embodiments, where modeling indicates that a particular user 160 is more likely to move rapidly toward a patient 110 in response to an alarm, a rule 250 may be established indicating for such motion to be interpreted as an acknowledgement by that particular user 160 without the user 160 having to explicitly acknowledge the alarm on their user mobile device 150. Various other examples of applying rules for interpreting user responses may be implemented according to various embodiments. Some of these example embodiments are discussed with respect to FIG. 7. The alarm management system 130 may also apply the models and rules 250 to identify when a user 160 is not responding as expected and then respond by escalating the alarm presentation to that user 160 (e.g. make it louder and louder) or shifting the alarm presentation to another user 160 who may be known to be available, physically close the patient 110, or otherwise a preferred candidate for addressing the alarm.

In block 570, the alarm management system 130 can update models and rules to improve alarm efficacy and/or patient outcomes. Accordingly, the models and rules may be adaptive to seek improvement through the implementation of various machine-learning techniques known in the machine intelligence arts such as applying iterative error reduction, minimum mean square error, gradient descent, simulated annealing, adaptive neural networks, retraining, and so forth to parameters associated with the various rules 250 of the alarm management system 130. Updated or adapted rules 250 may be reintroduced into the rule implementation system 200.

Figure 6:
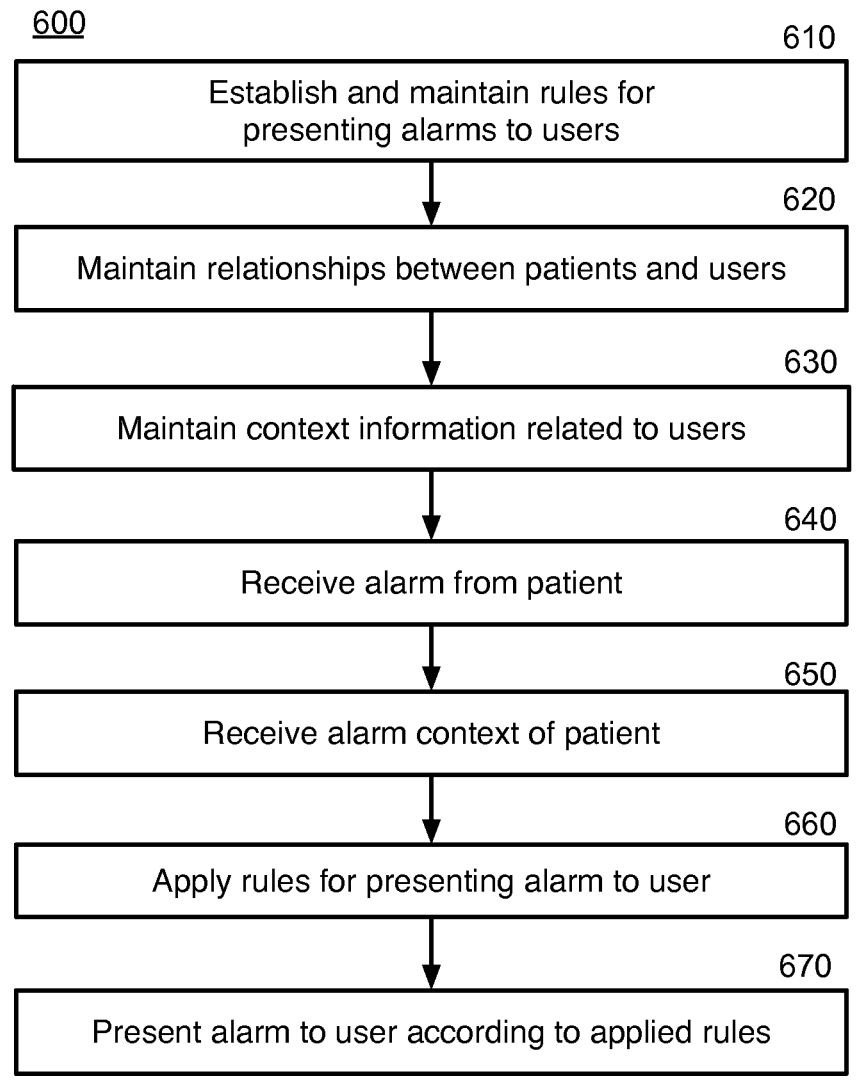
FIG. 6 is a block flow diagram depicting a method for the intelligent presentation of alarms within a healthcare enterprise in accordance with one or more embodiments presented herein.

FIG. 6 is a block flow diagram depicting a method 600 for the intelligent presentation of alarms within a healthcare enterprise in accordance with one or more embodiments presented herein. In block 610, the alarm management system 130 can establish and maintain rules for presenting alarms to users 160. These may be rules 250 such as those associated with the rule implementation system 200 and as discussed with respect to FIG. 5. Establishing and maintaining the rules 250 for presenting alarms to users 160 may be based upon modeling behaviors and patient outcomes as discussed with respect to FIG. 5. For example, the rules 250 may be established to reduce alarm fatigue. One example embodiment for reducing alarm fatigue may include multiple alarms (perhaps lower priority alarms) to the same user 160 being consolidated into fewer or even one single alarm event. As another example embodiment, alarms to a nurse user 160 for a particular patient 110 may be suppressed when the nurse user 160 is in the patient room or when a procedure is being performed on the patient 110. Various other rules 250 may be established within the alarm management system 130 to intelligently process and manage the presentation of alarms to users 160. Such intelligent processing can work to any specified modeling metric such as improving efficacy of the users 160, reducing costs, expediting discharges, improving patient outcomes, reducing patient readmissions, improving patient feedback on customer satisfaction surveys, or so forth. In general, the alarm management system 130 can seek to simplify the handling of alarms by the users 160. According to some embodiments, the alarm management system 130 may seek to predict alarms through detailed modeling.

In block 620, the alarm management system 130 can maintain relationships between patients 110 and users 160. This information may generally be obtained from electronic medical records systems or from user 160 roles and assignments. For example, a nurse user 160 may be assigned a certain number of patients 110 every shift. These relationships can indicate what user 160 should be routed alarms associated with specific patients 110 to which they are assigned. In addition to simple administrative shift assignments, users 160 may also be associated with particular patients 110 according to skill sets, location (physical proximity), current activity levels, current assignment load, and so forth. These factors may be used to route a particular alarm associated with a patient 110 to a user 160 who is particularly trained to handle that alarm, or a user 160 who happens to be walking past the patients room as an emergency condition arises, and so forth. Escalation rules and patterns may also be established for situations when a user 160 cannot or does not acknowledge an alarm. For example, a user 160 may have a backup user 160 (according to some examples, their supervisor) who will receive escalated alarms that they fail to respond to. These rules may also determine how to allocate a default backup in instances where a backup user 160 has not been explicitly specified. In other example embodiments, alarms may be directed to a care team of two or more users 160 as opposed to being allocated to a single user 160. Groups of users 160 may also be established by roles of the users 160 to form appropriate teams or care teams.

In block 630, the alarm management system 130 can maintain context information related to users 160. Such context information may involve where the user is and what they are doing. For example, the location and motion of the user 160 can indicate where the user is and to where they are moving. Roles, assignments, and recent alarms associated with a user 160 may indicate how busy they are and thus how available they may be to field a new alarm. Further context may indicate how the user 160 responds to various types of alarms given their other contextual information. For example, when working at the nurse station, a nurse user 160 may respond effectively to a simple textual message alarm notification, while the alarm management system 130 may have established through modeling that the same nurse user 160 responds most effectively to a noisy alarm tone while they are walking rapidly through the hallway.

In block 640, the alarm management system 130 can receive an alarm from patient 110. For example, medical devices 120 associated with the patient 110 can generate alarms or alarm indicators for a variety of reasons. Various other alarm generating conditions may apply.

In block 650, the alarm management system 130 can receive the alarm context of the patient 110 associated with the alarm. For example, additional information about the patient 110 may be received in association with the alarm. According to various examples, additional patient information may include conditions (e.g. cancer, cardiac, diabetic, dementia, etc.), age, recent alarms generated, medications, recent procedures, medical monitoring waveforms, medical imaging, current images, current video, voice intercom, and so forth.

In block 660, the alarm management system 130 can apply rules for presenting the alarm to the user 160. The alarm received in block 640 can be routed to a user 160. Whether the alarm gets routed, to whom it get routed, and how it is to be presented may all be determined by applying the rules 250 discussed in block 610. The rules 250 may be applied according to the rule implementation system 200 associated with the alarm management system 130. Application of the rules 250 may use as facts 260 or other parameters various information related to the received alarm from block 640, the user context discussed in block 630, the patient context discussed in block 650, and the relationship between the patient 160 and the user 110 as discussed in block 620.

The rules 250 may establish how the to alarm is to be presented to the user 160. Alarms may be presented at sounds or alarm tones played on the user mobile device 150. Alarms may also be presented as vibrations, flashing lights, graphical display, textual displays, animations, or any combination thereof. Alarm tones may comprise multiple ringtones. Users 160 may select alarm tones, or tones may be assigned according to functional criteria. For example, alarm tones may differ according to alert severity. Hands-free alarm presentation may be supported by voice annunciation where information about the alarm is presented at the user mobile device 150 using voice synthesis or recorded voice messages played through a speaker. For example "Attention. Patient Alarm in Room 941." Alarm presentation may evolve over time. For example, if a user 160 does not acknowledge an alarm after a period of time, the volume of the alarm may be increased or the alarm tone or presentation may be altered. The period of time before changing may be preset or may be learned through user modeling. The various styles of presentations as well as specific parameters (how to annunciate voice alarm, what volume to use, to use a tone or vibration, and so on) may be determined and fine-tuned using the behavioral and outcome modeling techniques presented herein. All of these factors may be implemented according to the established rules 250 associated with alarm presentation.

The rules 250 establishing how the to alarm is to be presented to the user 160 may also specify that the alarm is to be presented along with additional information or an option for the user 160 to request additional patient information associated with the alarm or the patient 110. Some examples of additional patient or alarm information are discussed with respect to block 650 and elsewhere herein.

Figure 7:
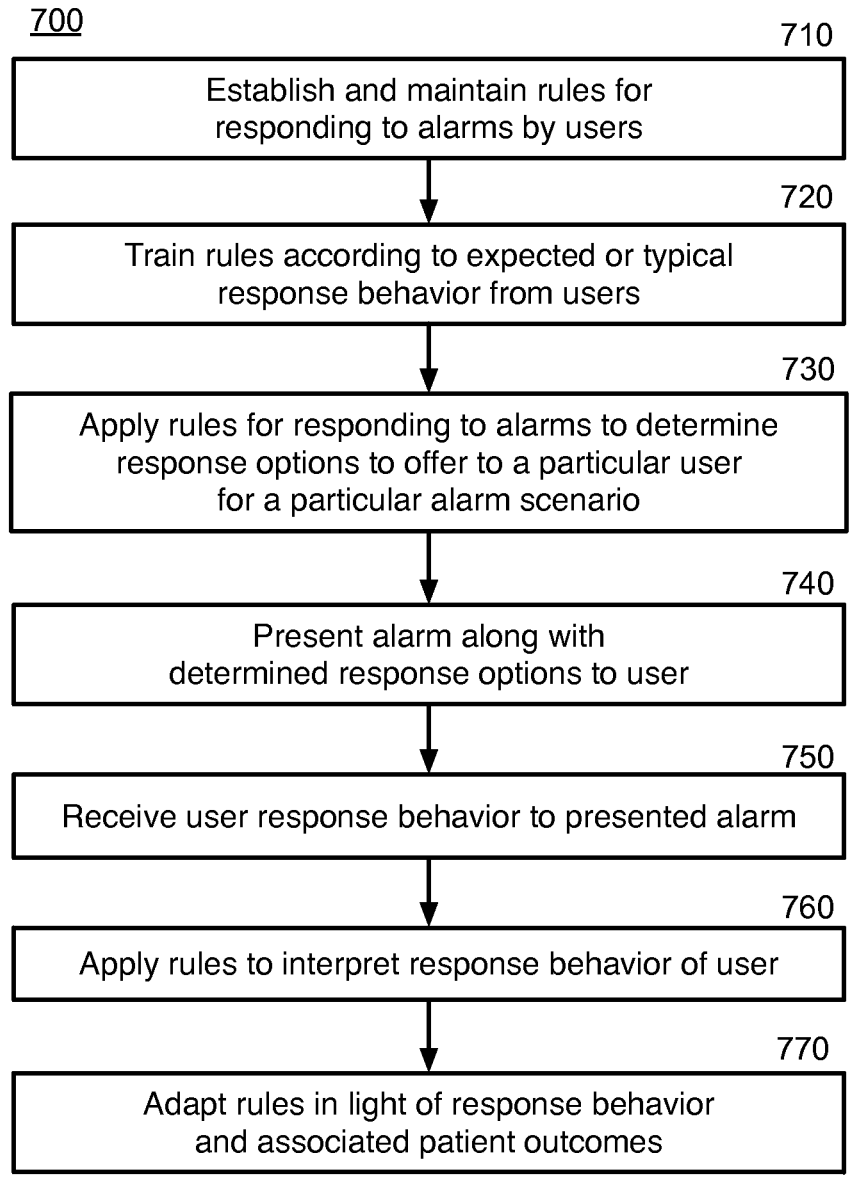
FIG. 7 is a block flow diagram depicting a method for augmented acknowledgment of alarms within a healthcare enterprise in accordance with one or more embodiments presented herein.

Another aspect of how the alarm may be presented to the user 160 can include how the alarm offers the user 160 to respond to or acknowledge the alarm as discussed with respect to FIG. 7. In general, acknowledgement or response to an alarm can include several variations upon rejecting the alarm, accepting the alarm, or query additional information associated with the alarm. Along with the other aspects of presenting alarms, these factors may be implemented according to the established rules 250 associated with alarm presentation, which may be determined and fine-tuned using the behavioral and outcome modeling techniques presented herein.

In block 670, the alarm management system 130 can present the alarm to the user 160 according to the applied rules 250 as discussed with respect to block 660. The alarm may be presented at the user mobile device 150, a desktop being used by the user 160, a wearable computing device associated with the user 160, a larger (possibly wall mounted) display proximate to the user 160, any other communication device, any other computing machine associated with or physically proximate to the user 160, or any combination thereof.

The alarm may be presented to the user 160 along with additional info related to the patient 110 or the alarm as discussed with respect to block 650. The alarm may also present with an option for the user 160 to query or request the additional information. The additional information may be textual information (for example, patient 110 heart rate, temperature, medication information). The additional information may also be visual, such as a waveform from a medical instrument, radiological imaging, image or video of the patient room, and so forth. When such a display is presented to the user mobile device 150, it may be windowed and explored with sliders such that it may be displayed at full resolution. Such a display may also be relayed to a larger monitor or computer display system that is physically proximate to the user 160. Such proximity may be ascertained using the location functionality of the user mobile device 150.

FIG. 7 is a block flow diagram depicting a method 700 for augmented acknowledgment of alarms within a healthcare enterprise in accordance with one or more embodiments presented herein. In block 710, the alarm management system 130 can establish and maintain rules for users 160 responding to, or acknowledging, alarms. These may be rules 250 such as those associated with the rule implementation system 200 and as discussed with respect to FIG. 5. Establishing and maintaining the rules 250 for users 160 responding to alarms may be based upon modeling behaviors and patient outcomes as discussed with respect to FIG. 5. For example, the rules 250 may be established to reduce alarm fatigue or to work to any specified modeling metric such as improving efficacy of the users 160, reducing costs, expediting patient discharge, improving patient outcomes, reducing patient readmissions, improving patient feedback on customer satisfaction surveys, or so forth. In general, the alarm management system 130 can seek to simplify the handling of alarms by the users 160. According to some embodiments, the alarm management system 130 may seek to predict alarms, and reactions thereto, through detailed modeling.

The rules 250 related to user response to alarms can determine the options for responding to an alarm that are presented to the user 160 along with the alarm. A simple example would allow the user 160 to hit a button (or make some other input) to acknowledge that they have received the alarm. A slightly more complex example might allow the user 160 to accept or reject the alarm. Other examples may allow the user 160 to forward the alarm to another specific user 160, to speak with the patient 110, to view the patient 110, to request more information about the patient 110 or the nature of the alarm, and so forth.

Additional examples of rules 250 for responding to alarms address various options for the user 160 to accept the alarm, reject the alarm, forward the alarm, send a message related to the alarm, establish an audio/voice connection to the patient 110, or view an instrument waveform (or medical imaging, lab results, patient video surveillance, patient image surveillance, or other display) associated with the alarm and/or the patient 110.

Further examples of rules 250 for responding to alarms address various options for the user 160 to respond to an alarm (explicitly or implicitly) by their location or motion. For example, a user 160 being in the room with the patient 110 may cause the alarm to be automatically accepted by that user 160. A similar rule may be used when the user 160 is in motion, moving into or towards the patient 110. On the contrary, if modeling of user behavior, assignment, previous alarms, or other information indicates that the user 160 is in another location away from the patient 110, is busy, and is not moving toward the patient, a response rejecting the alarm may be inferred.

Additionally, rules 250 for responding to alarms may address various options for the user 160 to issue or establish a communication with another user 160, the patient 110, or one or more other individuals as part of their response to an alarm. For example, the user 160 may accept the alarm while also generating a quick message. The message may be entered as text, speak, or select from a preexisting list. As an alternative example, the user 160 may forward the alarm to another user 160 along with such a message. According to yet other examples, the user 160 may be able to initiate surveillance of the patient room using video, still images, audio, or any combination thereof. Also, the user 160 may be able to establish a voice or video call with another user 160, the patient 110, or one or more other individuals regarding the alarm.

Additionally, rules 250 for responding to alarms may address various options for the user 160 to request additional information about the alarm or the patient 110. For example, the user 160 may be provided options for taking another measurement, taking a different measurement, changing the frequency of monitoring, order tests/labs, request medical imaging, and so forth. Other examples may support patient information, or additional requested information, to be forwarded to another clinician.

In block 720, the alarm management system 130 can train the rules 250 according to expected or typical response behavior from the users 160. The rules 250 can adapt to best manage alarm response according to one or more of various metrics. Example metrics may include how rapidly users 160 acknowledge alarms, reduction in ignored alarms, percentage of alarms get accepted over rejected, how rapidly or correctly the user 160 addresses the need of the patient 110, user 160 stress reduction, patient health outcomes, patient satisfaction outcomes, cost reductions, readmission reductions, discharge facilitations, and so forth.

The training or adaptation of the rules 250 can support the alarm management system 130 in managing alarm responses in a fashion that has been learned or adapted by the system to improve user 160 reactions or otherwise assist the user 160 in effectively handing alarm notices. The training or adaptation of the rules 250 can also support the alarm management system 130 in determining when the user 160 is not responded as expected or as they usually do. This determination can serve as a response in itself. For example, if a particular user 160 generally acknowledges alarms within 45 seconds and in a certain instance, 60 seconds have passed without acknowledgement, the alarm management system 130 may determine that the user 160 is unavailable. At that time, the alarm management system 130 may proceed to forward the alarm to another user 160, escalate it to a supervisor, or take some other course of action. According to other examples, the alarm management system 130 may attempt to use a modified alarm tone after the typical tone was not acknowledged. If the response time of the user 160, while hearing the modified tone, is less than the user's usual time, then the alarm management system 130 may learn to use the modified tone as the primary tone for the user 160 going forward.

According to other examples, the alarm management system 130 can learn a typical response time for that user 160 (or a category of users 160) and when the typical time is exceeded by some margin, the alarm device can replay a slightly perturbed version of the alarm tone in an attempt to get the attention of the user 160. Example modifications to the tone may include using the same musical composition in a different key, using the same tone played significantly faster, using the same musical key in a different composition, using the same tone played at a different speed, increasing the amplitude, or modulating the amplitude, and so forth. For example, the second alarm tone may be similar to the primary alarm tone, but altered in such a way that the user will recognize the tone but perceive it as different from the alarm tones that may be ignored as a result of hearing them repeatedly many times each day. Such changes may only need to be different enough to break through any alarm fatigue from the user 160. Similarly, the alarm tones may be replayed at random or varying intervals to confuse the user 160 away from ignoring the alarm or thus avoiding alarm fatigue.

In block 730, the alarm management system 130 can apply rules 250 to determine response options to offer to a particular user 160 for a particular alarm scenario or context. The rules 250 may be those associated with users 160 responding to alarms as established in block 710. The rules 250 may be applied by the rule implementation system 200 associated with the alarm management system 130 to determine which options for response should be offered to the user 160 via the user mobile device 150 when presenting an alarm to the user 160. In block 740, the alarm management system 130 can present an alarm to a user 160 along with one or more response options as determined in block 730.

In block 750, the alarm management system 130 can receive response behavior from a user 160 associated with the presentation of the alarm in block 740. The response behavior may include explicit responses such as acting on the response options discussed with respect to block 730. For example, the user 160 may click to accept or reject the alarm, request addition information, forward the alarm, or so forth. According to other examples, the response behavior may be implied such as the user 160 suddenly moving towards the patient 110, or an implied rejection/escalation from the user 160 doing nothing at all.

In block 760, the alarm management system 130 can apply rules 250 to interpret the response behavior received from the user 160 in block 750. The response of the user 160 to an alarm may be interpreted in relation to the context of the patient 110, the context of the user 160, the context of the alarm, learned use patters, and so forth. The response to be interpreted may be explicit or implied. In block 770, the alarm management system 130 can adapt the rules 250 in light of the response behavior and/or associated patient outcomes.

Figure 8:
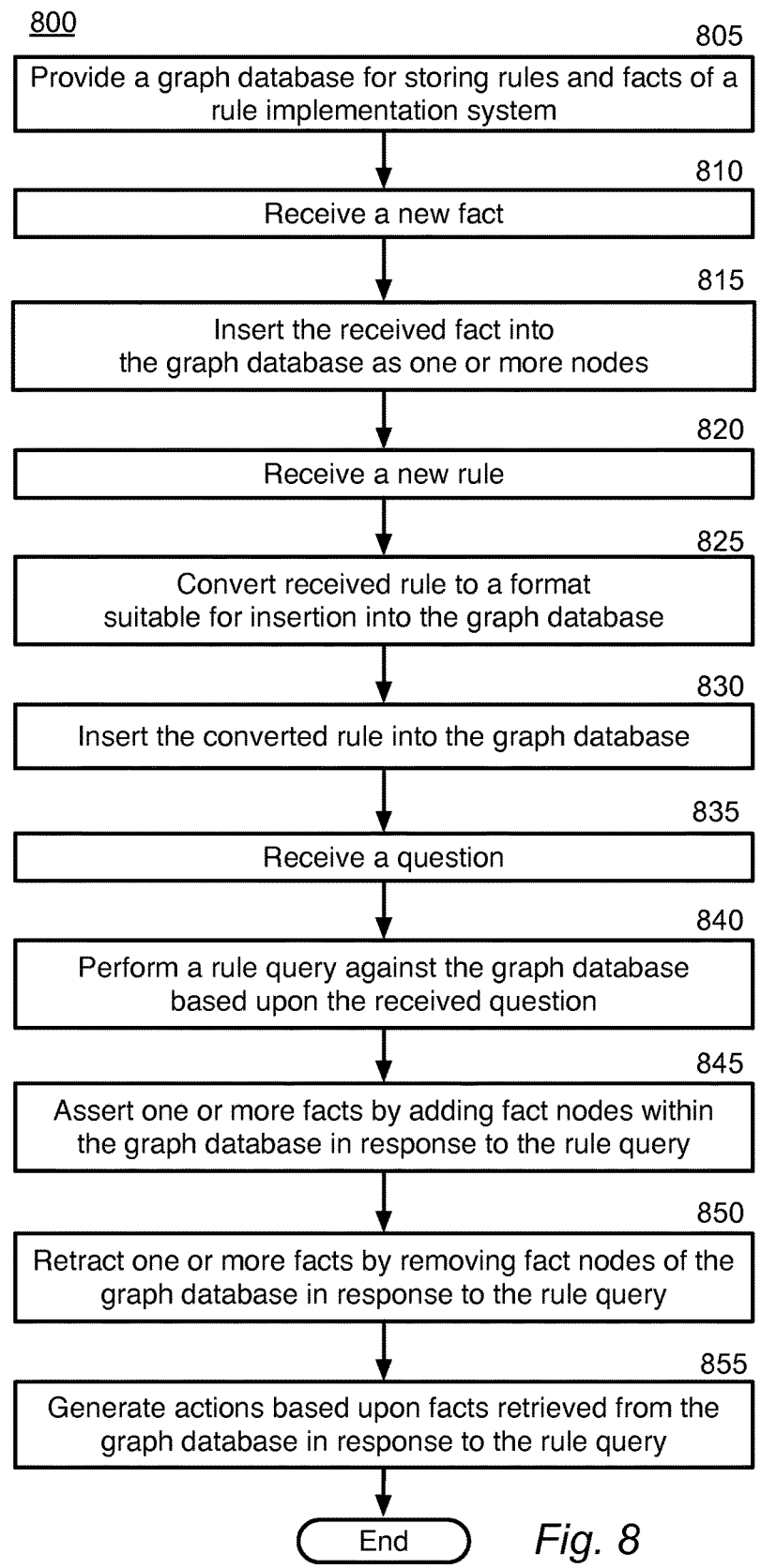
FIG. 8 is a block flow diagram depicting a method for efficient graph-based rule engines leveraging graph databases in accordance with one or more embodiments presented herein.

FIG. 8 is a block flow diagram depicting a method 800 for efficient graph-based rule engines leveraging graph databases 240 in accordance with one or more embodiments presented herein. The rule implementation system 200 may be any rule engine system, production system, production rule system, or other solution such as those used in artificial intelligence, machine based knowledge, expert system, or decision systems. Example embodiments leveraging graph databases 240 and/or complex event handlers are not intended to limit the possible implementation of the rule implementation system 200.

The rule implementation system 200 can implement the alarm processing associated intelligence associated with the alarm management system 130. In block 805, the rule implementation system 200 can provide a graph database 240 for storing rules 250 and facts 260 and responding to questions 265. The graph database 240 can provide persistence of the rules 250 and facts 260 associated with the rule implementation system 200.

In block 810, the rule implementation system 200 can receive a new fact 260 via the interface module 210. The interface module 210 can provide an API, scripting interface, DSL, or other mechanism for interfacing to the rule implementation system 200.

In block 815, the database translation module 130 of the rule implementation system 200 can insert the received fact 260 into the graph database 240 as one or more nodes 310

In block 820, the rule implementation system 200 can receive a new rule 250 via the interface module 210. The interface module 210 can provide an API, scripting interface, DSL, or other mechanism for interfacing to the rule implementation system 200.

In block 825, the rule implementation system 200 can convert the received rule 250 to a format suitable for insertion into the graph database 240. For example, the rule 250 may be converted to one or more nodes 310 and one or more edges 320.

In block 830, the database translation module 130 of the rule implementation system 200 can insert the converted rule 250 into the graph database 240. Rules 250 may be inserted by adding one or more nodes 310 to the graph database 240 and then forming one or more edges 320 between newly inserted nodes 310 or existing nodes 310. These edges 320 establish relationship between the nodes 310 which may represent facts 260. For example, the rule "all ravens are black," might be represented in the graph database 240 by creating nodes 310 for "ravens" and "black" followed by connecting those nodes 310 with an edge 320 having the property or implication of "is" or "are." Were this same example rule received while nodes 310 for "ravens" and "black" already exist, then the rule may be entered by merely forming the relationship edge 320 between those two nodes.

In block 835, the rule implementation system 200 can receive a question 265. In block 840, the rule implementation system 200 can perform a rule query against the graph database 240 in response to the received question 265. The question 265 may be pattern matched against facts and relationships stored within the nodes 310 and edges 320 of the graph database 240 by issuing a query to the graph database 240. In response to the query, various facts 260 may be reported, facts and/or rules 250 may be asserted or retracted within the graph database 240, or actions 270 may be initiated by the triggering of rules 250. It should be appreciated that these questions 265 and related queries may relate to the operational rules for a healthcare information system such as those associated with voice communications, roles, alarms, and message of various actors such as nurses, technicians, physicians, specialists, or other clinical providers.

In block 845, the rule implementation system 200 can assert one or more facts 260 by adding one or more fact nodes 310 within the graph database 240 in response to the rule query of block 840.

In block 850, the rule implementation system 200 can retract one or more facts 260 by removing one or more fact nodes 310 of the graph database 240 in response to the rule query of block 840.

In block 855, the rule implementation system 200 can generate actions 270 based upon facts 260 retrieved from the graph database 240 in response to the rule query. Facts 260 can be retrieved from the graph database 240 via the interface module 210 or by using a native query language of the graph database 240. Actions 270 may also be based upon rules 250 triggered (or fired) with respect to the graph database 240 in response to the rule query.

Example Systems

FIG. 9 depicts a computing machine 2000 and a module 2050 in accordance with one or more embodiments presented herein. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a vehicular information system, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain embodiments, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 also may include volatile memories, such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attachment ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, biometric readers, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks ("WAN"), local area networks ("LAN"), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

In situations in which the systems discussed here collect personal information about users, or may make use of personal information, the users may be provided with a opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

One or more aspects of embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the invention should not be construed as limited to any one set of computer program instructions. Further, a skilled programmer would be able to write such a computer program to implement an embodiment of the disclosed invention based on the appended flow charts and associated description in the application text. Therefore, disclosure of a particular set of program code instructions is not considered necessary for an adequate understanding of how to make and use the invention. Further, those skilled in the art will appreciate that one or more aspects of the invention described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays ("FPGA"), etc.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of embodiments of the invention. Accordingly, such alternative embodiments are included in the inventions described herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of the invention defined in the following claims, the scope of which is to be accorded the broadest interpretation so as to encompass such modifications and equivalent structures.

What is claimed is:

1. A computer-implemented method for usage modeling and intelligent management of patient alarms, comprising:
   maintaining, in association with an alarm management system, models of patient alarm operations;
   incorporating, by the alarm management system, into the models of patient alarm operations one or more modeling parameters related to motion behaviors associated with clinical users;
   establishing a rule associated with intelligent alarm presentation, by the alarm management system, based upon the one or more modeling parameters related to motion behaviors associated with clinical users;
   receiving, by the alarm management system, an alarm indication;
   receiving, by the alarm management system, motion information associated with a respective one of the clinical users;
   applying the established rule associated with the intelligent alarm presentation and the received motion information, by the alarm management system, to presentation of the received alarm indication to the respective one of the clinical users; and
   adapting the established rule associated with the intelligent alarm presentation, by the alarm management system, to improve a metric of patient alarm response efficacy.

2. The computer-implemented method of claim 1, wherein the alarm management system comprises a rule engine and applying the rule comprises execution of rules with respect to the rule engine.

3. The computer-implemented method of claim 1, wherein the patient alarms are received by the alarm management system from one or more medical devices associated with one or more patients.

4. The computer-implemented method of claim 1, wherein the presentation of the received alarm indication to the respective one of the clinical users comprises transmitting alarm information to a mobile computing device associated with the respective one of the clinical users.

5. The computer-implemented method of claim 1, further comprising applying the rule to determine alarm response options to offer to the clinical users along with presentation of the patient alarms.

6. The computer-implemented method of claim 1, wherein the motion behaviors associated with the clinical users further comprises a change in motion associated with the clinical users.

7. The computer-implemented method of claim 1, wherein the motion behaviors associated with the clinical users further comprise a location associated with the clinical users.

8. The computer-implemented method of claim 1, wherein the motion behaviors associated with the clinical users further comprise a past alarm response time.

9. The computer-implemented method of claim 1, further comprising adapting the established rule to improve a metric of patient outcomes.

10. The computer-implemented method of claim 1, wherein the models comprise thresholds used when applying the established rule.

11. A medical alarm management system, comprising:
   one or more processing units, and one or more processing modules, wherein the medical alarm management system is configured by the one or more processing modules to:
   maintain models of patient alarm operations;
   incorporate, into the models of patient alarm operations, one or more modeling parameters related to motion behaviors associated with clinical users;
   establish a rule associated with intelligent alarm presentation based upon the one or more modeling parameters related to motion behaviors associated with clinical users;
   receive an alarm indication;
   receive motion information associated with a clinical user;
   apply the established rule associated with the intelligent alarm presentation and the received motion information to presentation of the received alarm indication to the clinical user; and
   adapt the established rule associated with the intelligent alarm presentation to improve a metric of patient alarm response efficacy.

12. The medical alarm management system of claim 11, wherein the medical alarm management system comprises a rule engine and applying the rule comprises execution of rules with respect to the rule engine.

13. The medical alarm management system of claim 11, wherein the patient alarms are received by the medical alarm management system from one or more medical devices associated with one or more patients.

14. The medical alarm management system of claim 11, wherein the presentation of the received alarm indication to the respective one of the clinical users comprises transmitting alarm information to a mobile computing device associated with the respective one of the clinical users.

15. The medical alarm management system of claim 11, wherein the medical alarm management system is further configured by the one or more processing modules to apply the rule to determine alarm response options to offer to the clinical users along with presentation of the patient alarms.

16. The medical alarm management system of claim 11, wherein the motion behaviors associated with the clinical users further comprises a change in motion associated with the clinical users.

17. The medical alarm management system of claim 11, wherein the motion behaviors associated with the clinical users further comprise a location associated with the clinical users.

18. The medical alarm management system of claim 11, wherein the motion behaviors associated with the clinical users further comprise a past alarm response time.

19. The medical alarm management system of claim 11, wherein the medical alarm management system is further configured by the one or more processing modules to adapt the established rule to improve a metric of patient outcomes.

20. A computer program product, comprising:
a non-transitory computer-readable storage medium having computer-readable program code embodied therein that, when executed by one or more computing devices, perform a method comprising:
maintaining models of patient alarm operations, where the patient alarms originate from medical devices associated with one or more patients;
incorporating, into the models of patient alarm operations, one or more modeling parameters related to motion behaviors associated with one or more clinical users;
incorporating one or more modeling parameters related to alarm context into the models of patient alarm operations;
establish rules associated with management of patient alarms based upon the models of patient alarm operations;
receive motion information associated with a clinical user;
applying the established rules associated with management of patient alarms and the received motion information to presentation of alarms to mobile devices associated with the clinical user;
applying the established rules associated with management of patient alarms to determine alarm response options to offer to the clinical user along with presentation of the patient alarms;
applying the established rules associated with management of patient alarms to interpretation of alarm responses from the clinical user;
adapting the established rules associated with management of patient alarms to improve a metric of patient alarm efficacy; and
adapting the established rules associated with management of patient alarms to improve a metric of patient outcomes.

* * * * *